US00PP28747P2

(12) United States Plant Patent
Hansen

(10) Patent No.: US PP28,747 P2
(45) Date of Patent: Dec. 5, 2017

(54) ***AGASTACHE* PLANT NAMED 'MANGO TANGO'**

(50) Latin Name: ***Agastache* hybrid**
Varietal Denomination: Mango Tango

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 63 days.

(21) Appl. No.: 14/999,484

(22) Filed: May 12, 2016

(51) Int. Cl.
*A01H 5/02* (2006.01)

(52) U.S. Cl.
USPC ..... Plt./399
CPC ..... *A01H 5/02* (2013.01)

(58) Field of Classification Search
USPC ..... Plt./399
See application file for complete search history.

(56) References Cited

PUBLICATIONS

Trademarks on "Tango Mango", trademark Nos. 87580554 filed Aug. 23, 2017 downloaded from http://tmsearch.uspto.gov/on Sep. 5, 2017.*
Trademark on "Tango Mango", trademark No. 87580201 filed Aug. 23, 2017, downloaded from http://tmsearch.uspto.gov/on Sep. 5, 2017.*

* cited by examiner

*Primary Examiner* — Anne M Grunberg

(57) ABSTRACT

A new and unique cultivar of hyssop plant, named *Agastache* 'Mango Tango' with compact, dense, rounded, well-branched habit. The flowers cover the top three-quarters of the plant, are large, light-peach to dusky-orange in color, in tightly clustered verticils over an extended period which is lengthened further by persistent dusky rose-colored calyxes.

1 Drawing Sheet

Botanical denomination: *Agastache* hybrid.
Variety designation: 'Mango Tango'.

BACKGROUND OF THE INVENTION

The present invention relates to the new and distinct plant cultivar of hyssop or anise hyssop from the genus *Agastache* and given the cultivar name 'Mango Tango'. The new plant was the result of a single seedling selection from an open-pollinated cross in the summer of 2011 by the inventor between the proprietary, unreleased, hybrid, clone *Agastache* HK10-17-01 (not patented) as the female or seed parent and an unknown parent from a mixed isolation bed as the male or pollen parent. The seeds from the pollination were collected in November of 2011. The individually selected seedling was eventually given the breeder code 11-18-02 after being first isolated from trials at a nursery in Zeeland, Mich. during the summer of 2012. It was selected for final introduction in the summer of 2013.

*Agastache* 'Mango Tango' has been asexually propagated at the same nursery in Zeeland, Mich. using traditional shoot tip and stem cutting procedures and found to reproduce plants that are identical and exhibit all the characteristics of the original plant in successive generations of asexual propagation.

No plants of *Agastache* 'Mango Tango' have been sold, in this country or anywhere in the world, prior to the filing of this application, nor has any disclosure of the new plant been made prior to the filing of this application with the except that which was disclosed within one year of the filing of this application and was either derived directly or indirectly from the inventor.

The new plant, *Agastache* 'Mango Tango', has not been observed under all possible environments. The phenotype may vary slightly with different environmental conditions, such as temperature, light, fertility, moisture and maturity levels, but without any change in the genotype.

In comparison to the seed parent, *Agastache* 'Mango Tango' is more compact and denser in habit and the flower color is more orange. The nearest comparison variety is 'Peachie Keen' U.S. Plant Pat. No. 25,886 which is not as compact or rounded in habit as the new plant, and 'Mango Tango' has a deeper shade of orange in the flowers than 'Peachie Keen'. Compared to *Agastache* 'Kudos Mandarin' U.S. Plant Pat. No. 25,381 the new plant has lighter colored flowers with less reddish tinting. Compared to *Agastache* 'Kudos Coral' U.S. Plant Pat. No. 25,613 the new plant has lighter colored flowers with more peach to dusky orange. Compared to *Agastache* 'Summer Sunset' U.S. Plant Pat. No. 23,623 the new plant is not as broad in habit, is more densely branched and the flower color contains more peach tinting.

The new plant *Agastache* 'Mango Tango' is distinct from the parents and all other anise hyssop known to the inventors in the following combined traits:

1. Compact, dense, rounded, well-branched habit;
2. Large flowers of light-peach to dusky-orange coloration in tightly clustered verticils;
3. Long bloom time with effectiveness extended by persistent dusky rose-colored calyxes;
4. Flowers covering the top three fourths of the plant.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, temperature, source and direction may cause the appearance of minor variation in color.

DETAILED PLANT DESCRIPTION

Figure 1:
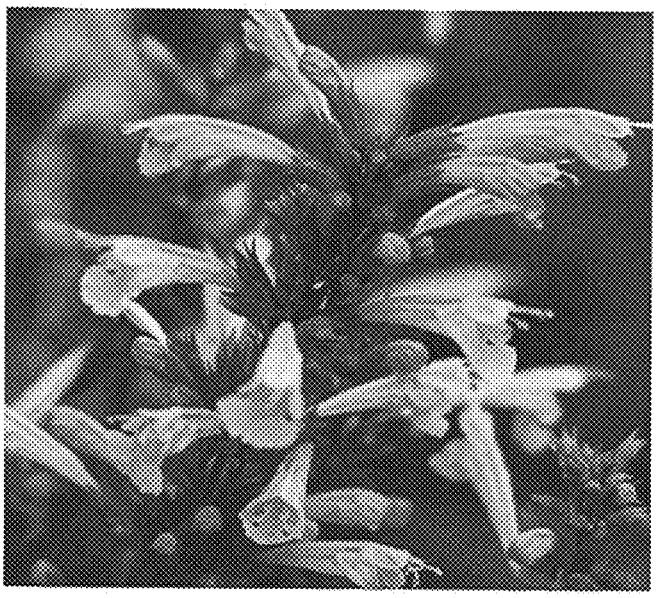
FIG. 1 shows a close-up of the scape with flowers, buds and calyxes.
Figure 2:
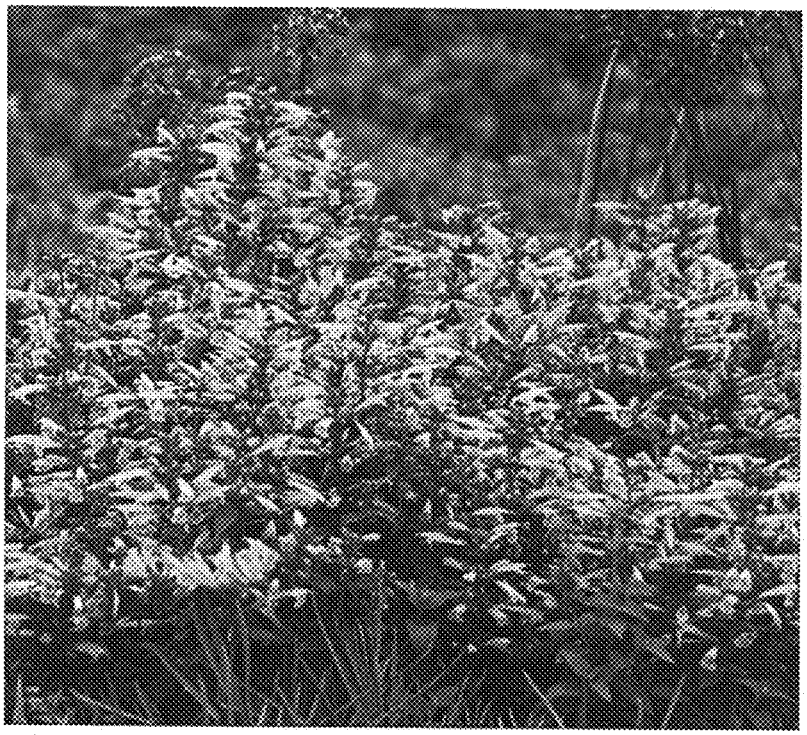
FIG. 2 shows a side view of two two-year-old plants side by side in mid-season flower in a trial block at a nursery in Zeeland, Mich.

The following is a detailed description of the new *Agastache* cultivar 'Mango Tango' based on observations of two-year old specimens grown with supplemental watering and fertilizer as needed in potted container trials in a lightly shaded greenhouse at a nursery in Zeeland, Mich. Color descriptions are from the 2001 edition of The Royal Horticultural Society Colour Chart except where common dictionary terms are used.

Plant habit: Multi-stemmed herbaceous perennial, rounded, heavily branched.

Plant size: Without growth retardants or pinching — about 32.0 to 45.0 cm tall and 32.0 to 45.0 cm across.

Roots: Fibrous; to about 2.0 mm diameter near base; color light tan nearest RHS 165D.

Stem: Quadrate in cross-section, stiff, wiry, finely pubescent; to about 4.0 mm across at base and 45.0 cm tall with flowering starting about 11.0 cm above soil; internodes vary from 2.0 to 5.0 cm long.

Primary branches: Quadrate; opposite; about eight per plant; to about 18.0 cm long and about 2.5 mm diameter at base.

Secondary branches: Quadrate; opposite; up to six per primary branch; to about 11.0 cm long and 1.0 mm diameter at base.

Leaf: Simple, opposite, crenate to serrate; deltoid to ovate, base truncate to rounded, apex acute; blade adaxial glabrous and matte, abaxial surface puberulent and matte.

Leaf size: To about 22.0 mm long and 16.0 mm across at base.

Leaf venation: Reticulate; glabrous adaxial, puberulent abaxial.

Leaf color: Adaxial between RHS 143A to RHS 138A; abaxial closer to RHS 138B than RHS 138C with tinting of nearest RHS 187B between veins.

Vein color: Adaxial nearest RHS 145A, abaxial RHS 147C.

Leaf fragrance: Moderately herbal, minty.

Petiole: Puberulent; concavo-convex; to 9.0 mm long and 1.0 mm across, average 7.0 mm long and 1.0 mm.

Petiole color: Adaxial nearest RHS 145A in center and nearest RHS 138A at margin; abaxial nearest RHS 138B; slight tinting abaxial and adaxial of nearest RHS 185A.

Inflorescence: In verticillate spikes of leaf axils and nodes above leaves; 3 to 14 flowers per branchlet; up to eight whorls per main stem, 90 flowers per whorl and 400 flowers per main stem; terminal flowering portion about 9.5 cm long and about 7.5 cm across; secondary terminal flowering portion about 6.5 cm long and about 7.5 cm across; each stem flowering for about 4 weeks but remain effective for about 6 weeks or more with strongly pigmented persistent calyxes.

Bloom period: July through frost in Zeeland, Mich.

Peduncle: Average about 40.0 cm tall and about 3.5 mm at base; puberulent; attitude upward.

Peduncle color: Between RHS 137C and RHS 138B in lower portion of stem; regions exposed to more intense light become tinted with nearest RHS 187 A.

Flower: Perfect; zygomorphic, tubular, bilabiate; in spikes and whorls in axils of leaves; 5 united sepals, 5-part corolla with 2 lips, upper lip 2-lobed and lower lip 3-lobed; about 27.0 mm long; individual flowers open for about 3 days; attitude outward to slightly upward.

Bud on day prior to opening: Arcuate; club-shaped to obelliptic; about 23.0 mm long, 6.0 mm tall and 4.5 mm wide just before the apex and 1.0 mm wide at base.

Bud color: Between RHS N25B and RHS 26A toward apex, lightening to between RHS 25C to RHS 25D toward base.

Petals: Puberulent outside, glabrous inside; upper and lower petals proximally fused forming tube in the basal 23.0 mm.

Upper 2-lobed petal: About 27.0 mm long and 5.0 mm across toward apex; lobes centrally cleft about 1.5 mm deep; lobe apices rounded, margin entire.

Lower 3-lobed petal: About 24.0 mm long, arcuate downward in distal 6.0 mm; central lower lip about 4.0 mm wide at lobe base, slightly reflex downward and flares to about 7.0 mm wide with a rounded apex and crenate margin; two side lobes of lower petal spread horizontally, about 18.0 mm long and 3.0 mm wide, with rounded apex and entire margin.

Petal color: Shortly after opening abaxial and adaxial nearest RHS 24B with four stripes continuing from filament attachment to base of petals of between RHS 31A and RHS 32B, adaxial margin nearest RHS 24B and center nearest RHS 25A, adaxial tube nearest RHS 23A, abaxial margin nearest RHS 24B and center nearest RHS 24A; mature flower color adaxial lower petal face nearest RHS 36D and center rib nearest RHS 68B with throat nearest RHS 68C, abaxial tube nearest RHS 39C and distal lobes between RHS 36D and RHS 29D.

Calyx: Entire, apex acute; five, base fused into tube; puberulent outside and glabrous inside; fused in basal 6.5 mm and distally separated in the last 2.0 mm; combined about 8.5 mm long and diameter about 2.5 mm.

Calyx color: With intense light developing to nearest RHS 64A distally and along veins with a base of nearest RHS 138B, with more shading or less intense light between RHS 144A and RHS 144D.

Gynoecium:

*Style*.—One, about 27.0 mm long and less than 0.5 mm diameter; terete; glabrous.

*Style color*.—Distally nearest RHS 72C before stigma and lightening proximally to near white, lighter than RHS 155D.

*Stigma*.—Split into two and curled back to an angle of about 170 degrees; each segment about 1.0 mm long and less than 0.5 mm diameter; tapering to a pointed apex.

*Stigma color*.—Nearest RHS 72C.

*Ovary*.—Superior; about 0.5 mm diameter.

*Ovary color*.—Between RHS 150D and RHS 150C.

Androecium:

*Stamen*.—Four in two pairs, exerted, adnate to the corolla.

*Filaments*.—Two longer and two shorter; paired and exerted; longer pair fused in the basal 21.0 mm and free in the proximal 9.0 mm; shorter pair fused in the basal 16.0 mm and free in the proximal 8.0 mm.

*Filament color*.—Younger flowers nearest RHS 63C; mature flowers nearest RHS 70B distally and RHS 70C proximally.

*Anthers*.—Dorsifixed, versatile, longitudinal; about 1.0 mm long and about 0.5 mm across.

*Anther color*.—Between RHS N79B and RHS N79B.

*Pollen*.—Abundant; color lighter than RHS 158D.

Fragrance: None detected.

Fruit: Two carpels.

Seed: Nutlet, four, flattened ovoid; about 2.0 mm long, 1.0 mm diameter and 0.5 mm thick.

Seed color: Nearest 202A.

Resistance: 'Mango Tango' is resistant to deer browsing but has not been tested or shown resistance to other pests and diseases common to *Agastache*. The new plant has survived USDA hardiness zones 6 to 10 but has not been tested yet beyond these temperatures.

The invention claimed is:

1. The new and distinct cultivar of *Agastache* plant 'Mango Tango' as herein described and photographed.

* * * * *